US008824628B2

(12) United States Patent
Dolazza et al.

(10) Patent No.: US 8,824,628 B2
(45) Date of Patent: *Sep. 2, 2014

(54) METHOD OF AND APPARATUS FOR CONTINUOUS WAVE TOMOSYNTHESIS USING PHOTON COUNTING

(71) Applicant: Analogic Corporation, Peabody, MA (US)

(72) Inventors: Enrico Dolazza, Boston, MA (US); Sorin Marcovici, Lexington, MA (US); Wei Zhao, East Setauket, NY (US); Jonathan Greenspan, Quebec (CA); Luc Laperriere, Quebec (CA); Olivier Tousignant, Quebec (CA)

(73) Assignee: Analogic Corporation, Peabody, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/933,704

(22) Filed: Jul. 2, 2013

(65) Prior Publication Data
US 2013/0294573 A1 Nov. 7, 2013

Related U.S. Application Data

(63) Continuation of application No. 13/131,278, filed as application No. PCT/US2008/084955 on Nov. 26, 2008, now Pat. No. 8,477,901.

(51) Int. Cl.
*A61B 6/03* (2006.01)
*A61B 6/00* (2006.01)

(52) U.S. Cl.
CPC .................................. *A61B 6/4241* (2013.01)
USPC .................................. 378/22; 378/5; 382/131

(58) Field of Classification Search
CPC ...... A61B 6/482; A61B 6/025; A61B 6/4241; A61B 6/502; G01N 2223/423; G06T 2207/30068; G06T 2211/408; G06T 2211/436; H04N 5/32

USPC .................................. 378/5, 21–28; 382/131
See application file for complete search history.

(56) References Cited

U.S. PATENT DOCUMENTS 4,736,369 A 4/1988 Barzilai et al.
6,408,050 B1 * 6/2002 Han et al. ..................... 378/98.9
(Continued)

FOREIGN PATENT DOCUMENTS

JP 2003038482 A 2/2003
JP 2007050264 A 3/2007
(Continued)

OTHER PUBLICATIONS

Preliminary Amendment cited in U.S. Appl. No. 13/131,278 dated May 26, 2011, 9 pgs.
(Continued)

*Primary Examiner* — Toan Ton
*Assistant Examiner* — John Corbett
(74) *Attorney, Agent, or Firm* — Cooper Legal Group LLC

(57) ABSTRACT

Tomosynthesis data may be acquired from an ionizing radiation source that substantially continuously emits radiation while its position is varied relative to a photon counting detector. The detector detects photons comprised within the radiation and photon data indicative of the detected photons is generated. The photon data may comprise data related to a detected photon's detection time, detection location on the detector, energy level, and/or trajectory from the radiation source, for example. The photon data of various photons may be compiled into a plurality of bins and, through reconstruction and tomosynthesis techniques, produce synthesized images of various tomography planes of an object under examination. In this way, the tomosynthesis techniques rely on counting photons rather than measuring their energy to create synthesized images.

20 Claims, 5 Drawing Sheets

(56) References Cited

U.S. PATENT DOCUMENTS

| | | |
|---|---|---|
| 2003/0043962 A1 | 3/2003 | Lai |
| 2005/0113685 A1* | 5/2005 | Maschke et al. ............... 600/427 |
| 2005/0220265 A1 | 10/2005 | Besson |
| 2007/0019784 A1* | 1/2007 | Ting ................................ 378/21 |
| 2007/0269000 A1 | 11/2007 | Partain et al. |
| 2008/0317200 A1 | 12/2008 | Lecomte et al. |
| 2009/0161816 A1 | 6/2009 | De Man et al. |

FOREIGN PATENT DOCUMENTS

| | | |
|---|---|---|
| JP | 2007130487 A | 5/2007 |
| JP | 2007296337 A | 11/2007 |
| JP | 2008104878 A | 5/2008 |
| JP | 2009192490 A | 8/2009 |
| WO | 2007058600 A1 | 5/2007 |
| WO | 2007066243 A2 | 6/2007 |
| WO | WO 2008093275 A2 * | 8/2008 |

OTHER PUBLICATIONS

Non-Final Office Action cited in U.S. Appl. No. 13/131,278 dated May 25, 2012, 34 pgs.
Reply Non-Final Office Action cited in U.S. Appl. No. 13/131,278 dated Aug. 27, 2012, 14 pgs.
Final Office Action cited in U.S. Appl. No. 13/131,278 dated Dec. 6, 2012, 44 pgs.
Reply Final Office Action cited in U.S. Appl. No. 13/131,278 dated Feb. 16, 2013, 16 pgs.
Notice of Allowance cited in U.S. Appl. No. 13/131,278 dated Feb. 26, 2013, 16 pgs.
Notice of Allowance cited in U.S. Appl. No. 13/131,278 dated Apr. 10, 2013, 6 pgs.
Notice of Allowance cited in U.S. Appl. No. 13/131,278 dated May 17, 2013, 5 pgs.
Amendment after Notice of Allowance cited in U.S. Appl. No. 13/131,278 dated May 28, 2013, 12 pgs.
Reply to Amendment after Notice of Allowance cited in U.S. Appl. No. 13/131,278 dated Jun. 7, 2013, 4 pgs.
Int. Search Report cited in PCT Application No. PCT/US2006/084955 dated Feb. 27, 2009, 14 pgs.
First Chinese Office Action cited in Chinese Application No. 200880132121.4 dated Nov. 16, 2012, 13 pgs.
Reply first Chinese Office Action cited in Chinese Application No. 200880132121.4 dated Apr. 1, 2013, 4 pgs.
Second Chinese Office Action cited in Chinese Application No. 200880132121.4 dated Jul. 4, 2013, 10 pgs.
Japanese Office Action cited in Japanese Application No. 2011-538594 dated Jan. 9, 2012, 5 pgs.
"Evaluation of a photon-counting breast tomosynthesis imaging system", Andrew D.A.Maidment, Christer Ullberg, Karin Lindman, Leif Adelow, Johan Egerstrom, Mathias Eklund, Tom Francke, Ulf Jordung, Tomas Kristofferson, Lars Lindqvist, Daniel Marchal, Hans Olla, Erik Penton, Juha Rantanen, Skiff Solokov, Nielas Weber, and Hans Westerberg, 2006, Proceedings of SPIE, vol. 6142, Physics of Medical Imaging 11 pgs.
"Detection and characterization of breast tumours by time-domain scanning optical mammography", H. Rinneberg, D. Grosenick, K.T. Moesta, H. Wabnitz, J. Muche, G. Wubbeler, R. MacDonald and P. Schlag, Opto-Electronics Review, 16, No. 2, 2008, pp. 147-162.
"Single photon counter for digital x-ray mammography tomosynthesis", Amir H. Goldan, Karim S. Karim and John A. Rowlands, May/Jun. 2006 American Vacuum Society, J. Vac Science Technology, 854-859.
"Digital Tomosynthesis in Breast Imaging", Loren T. Nikiason et al., Nov. 1998, American College of Radiology, vol. 205, No. 2, pp. 399-406.
"Image Quality in Extended Arc Filtered Digital Tomosynthesis", C. Badea, Z. Kolitsi and N. Pallikarakis, Acta Radiologica 42, published Oct. 23, 2000, pp. 244-248.
"Initial application of digital tomosynthesis with on-board imaging in radiation oncology", Alan H. Baydush et al., Proceedings of SPIE, vol. 5745, Medical Imaging 2005, pp. 1300-1305.
"An ultra fast electron beam x-ray tomography scanner", F. Fischer, D. Hoppe, E. Schleicher, G. Mattausch, H. Flaske, R. Bartel and U. Hampel, Measurement Science and Technology, 2008, pp. 1-11.

\* cited by examiner

METHOD OF AND APPARATUS FOR CONTINUOUS WAVE TOMOSYNTHESIS USING PHOTON COUNTING

RELATED APPLICATION

This application is a continuation of U.S. patent application Ser. No. 13/131,278, filed on May 26, 2011, entitled "METHOD OF AND APPARATUS FOR CONTINUOUS WAVE TOMOSYNTHESIS USING PHOTON COUNTING" which is a national phrase entry of International Application No. PCT/US2008/084955, filed Nov. 26, 2008, entitled "METHOD OF AND APPARATUS FOR CONTINUOUS WAVE TOMOSYNTHESIS USING PHOTON COUNTING," and at least some of the U.S. application and/or the International application may be incorporated herein.

BACKGROUND

The present application applies to a method and apparatus for acquiring data that may be synthesized through tomosynthesis. Tomosynthesis ordinarily provides means for two-dimensional (2-D) images of an object, taken at a plurality of angles, to be combined and synthesized into a plurality of 2-D images that represent various tomography planes (e.g., slices) of the object. While the techniques disclosed herein may be applied in a variety of fields, they find particular application in the medical field.

Radiation devices, in general, provide a means for generating 2-D images of an object under examination. The object is exposed to radiation, and a 2-D image is formed based upon the radiation absorbed by the object, or rather a level of radiation (e.g., energy) that is able to pass through the object. Highly dense objects absorb more radiation than less dense objects, and thus an object having a higher density, such as a mass (e.g., a benign cyst or tumor), for example, will be apparent when surrounded by less dense objects, such as fatty tissue or muscle. In medical systems, radiation devices are commonly used to detect broken bones, masses, calcium deposits, etc. that are ordinarily not visible.

A radiation device typically comprises a detector array and a radiation source mounted on a diametrically opposing side of the object from the detector array, where the radiation source emits radiation toward the object. In digital radiology, digital pixels (of the detector array) detect radiation that traverses the object, and reconstruction algorithms create 2-D images of the object in the latitudinal dimension (e.g., orthogonal to a center ray and parallel to the detector array) based upon the energy of photons comprised in the detected radiation.

While 2-D images are useful in some applications, such as to detect a broken bone, the 2-D images are less useful for other procedures, such as breast cancer detection, because the images have no resolution in the longitudinal dimension (e.g., parallel to the center ray and orthogonal to the detector array). On a breast examination, for example, the 2-D images cannot provide information about whether a mass has ramified (e.g., spread to ducts in the breast and is likely to be malignant) in a longitudinal direction. Additionally, a less dense, but potentially cancerous mass, for example, may be masked by a more dense target, such as scar tissue, if the mass and scar tissue have similar latitudinal coordinates (e.g., one target is on top of the other).

Digital tomosynthesis, as described in U.S. Pat. No. 6,960,020 to Lai, enables a substantially three-dimensional (3-D) view of an object to be constructed from a finite set of 2-D images of the object. Typically, in digital tomosynthesis systems, the position of the radiation source is varied during data acquisition (with respect to the detector array and/or the object), for example in an arc through a limited angular range, and a set of projections of the object are acquired. A projection may represent data related to radiation emitted while the radiation source was at a predetermined point along the arc (e.g., a tomosynthesis view of the object). The set of projections may be converted into a set of 2-D images (through reconstruction) and combined and/or filtered, using digital tomosynthesis algorithms, to produce a certain degree of resolution in the longitudinal dimension of the object. That is, a set of synthesized 2-D images may be produced representing a plurality of tomography planes (e.g., slices) of the object. It will be appreciated that the number of synthesized 2-D images may be a function of the number of tomosynthesis views of the object. For example, a larger number of tomosynthesis views may promote a higher resolution in the longitudinal direction so the synthesized images may depict thinner tomography planes without the image becoming distorted because of smearing.

While current tomosynthesis acquisition techniques (e.g., based upon 2-D images acquired by measuring photon energy of the detected radiation) have proven effective in some instances, there remains room for improvement. The number of 2-D images (depicting a variety of tomosynthesis views) acquired by the apparatus is limited because the measure of radiation energy adds an amount of electronic noise (e.g., more tomosynthesis views add more electronic noise). While it is desirable to portion the examination dose over a large number of tomosynthesis views (thus allowing a higher longitudinal resolution), because electronic noise is additive (for each additional tomosynthesis view) the number of views is limited to provide a signal-to-noise ratio above some threshold. Additionally, the angular separation between tomosynthesis views (e.g., the number of degrees the radiation source is rotated) is restricted to promote image quality and/or reduce reconstruction artifacts. Therefore, the number of tomosynthesis views that allow a signal-to-noise ratio above some threshold (e.g., twenty views) and a permissible angular separation there-between (e.g., two degrees) define an allowable tomosynthesis angle (e.g., ±twenty degrees from center). This may, however, be less than ideal where, for example, a greater angle is desired (e.g., ±forty degrees from center).

Current tomosynthesis procedures also rely upon the radiation source travelling along a predetermined trajectory at a relatively slow, continuous speed while radiation is pulsed (e.g., emitted at predetermined points along the trajectory) to generate the images. While a faster speed may decrease the probability of reconstruction artifacts (due to a patient's movement), a faster speed (without reducing pulse duration) may also cause a virtual "elongation" of the focal spot of the radiation source and/or a tangential defocusing (e.g., poor focus) of the synthesized image, thereby reducing image quality. While the virtual "elongation" may be partially cured by increasing power to the radiation source, increasing the power also causes the size of actual focal spot to increase and the quality of the images to decrease. Therefore, the size of actual focal spot and the virtual "elongation" of the focal spot are balanced to improve image quality.

SUMMARY

Aspects of the present application address the above matters, and others. According to one aspect, an apparatus comprises an examination region configured to selectively receive an object under examination, an ionizing radiation source, and a photon counting x-ray detector that detects x-rays from the ionizing radiation source that have traversed the object (e.g., so as to substantially eliminate electronic noise). The apparatus also comprises a drive configured to vary, during an examination of the object, the relative position of the ionizing radiation source and the x-ray detector along a trajectory having an angular range of less than about sixty to about one hundred twenty degrees. The apparatus further comprises a photon data processor configured to generate photon data indicative of the location and detection time of each of a plurality of x-rays detected by the x-ray detector during the examination of the object.

According to another aspect, a tomosynthesis method is provided. The method comprises varying the relative position of an x-ray source and a photon counting x-ray detector during a tomosynthesis examination of an object while substantially continuously emitting x-rays from the x-ray source. The method also comprises generating photon data indicative of x-ray photons detected during the examination, wherein the photon data comprises a detection location and a detection time for each of a plurality of the detected photons. The method further comprises combining the photon data into a first plurality of bins using a pertinent signal processing to generate first binned data, using the first binned data to generate first tomosynthesis data indicative of the object, and presenting the first tomosynthesis data in human perceptible form.

According to another aspect, a method for generating tomosynthesis image data is provided. The method comprises, while varying the relative position of an x-ray source and a pixelated x-ray detector along a trajectory, substantially continuously emitting x-rays from the x-ray source. The method also comprises determining detection times and detection locations of x-rays detected by the x-ray detector and correlating the determined detection times with locations along the trajectory to create a plurality of projections. The method further comprises processing the plurality of projections to generate tomosynthesis image data indicative of an object under examination.

Those of ordinary skill in the art will appreciate still other aspects of the present application upon reading and understanding the appended description.

FIGURES

The application is illustrated by way of example and not limitation in the figures of the accompanying drawings, in which like references indicate similar elements and in which.

DESCRIPTION

Figure 1:
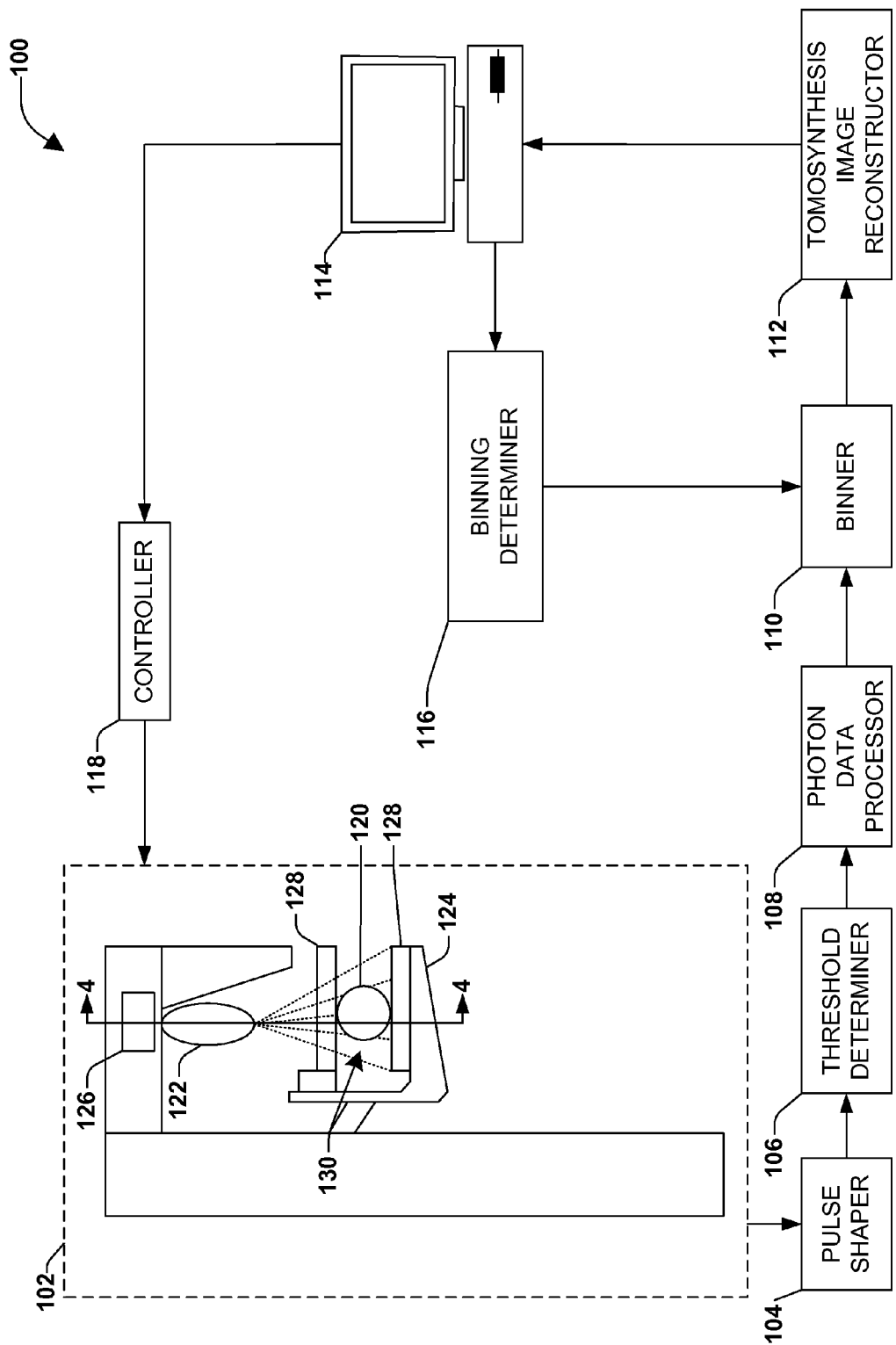
FIG. 1 is a schematic block diagram illustrating an example scanner wherein one or more of the provisions set forth herein may be implemented.

FIG. 1 depicts an example scanner 100. The scanner 100 may be used to scan tissue at a medical center, for example.

An object scanning apparatus 102 portion of the example scanner 100 is configured to scan an object 120 under examination and typically comprises an ionizing radiation source 122 and a pixelated photon counting x-ray detector 124. The ionizing radiation source 122 is configured to emit fan, cone, wedge, or other shaped radiation configuration into an examination region 130 that is configured to selectively receive the object 120. Radiation that traverses the object 120 in the examination region 130 is detected by the detector 124 located on a substantially diametrically opposing side of the object 120 from the ionizing radiation source 122.

The pixelated detector 124 is configured to detect photons comprised within the radiation. Targets (e.g., masses, scar tissue, etc.) within the object 120 (e.g., human tissue) may cause various amounts of photons to traverse the object 120 (e.g., creating areas of high traversal and areas of low traversal within the object). For example, fewer photons may traverse targets with a higher density (relative to densities of other targets in the object 120). It will be appreciated that the changes in traversal may be used to create images of targets within the object 120. For example, if human tissue is scanned by the object scanning apparatus 102, regions of tightly compacted cells may appear more prominently (or otherwise more discernable) on an image than healthy tissue cells (which may be virtually invisible).

The pixelated photo counting x-ray detector 124 may comprise any material capable of detecting photons. For example, the detector 124 may comprise a direct conversion x-ray detector material, such as a crystalline material and/or an amorphous photoelectric material. Additionally, the detector 124 may comprise a scintillator and a two-dimensional array of photodiodes configured to receive photons generated by the scintillator in response to radiation from the ionizing radiation source 122.

The object scanning apparatus 102 may also comprise a drive mechanism 126 configured to vary the relative position of the ionizing radiation source 122 and the detector 124 along a trajectory. Generally, the drive mechanism 126 is configured to vary their relative positions about an angular range of thirty to forty degrees, but may vary their relative positions about an angular range of less than about 60 to about 120 degrees (depending upon the geometry of the object scanning apparatus 102). It will be appreciated that the ionizing radiation source 122 and the detector 124 may move independently and/or in cooperation with one another. In one example, the detector 124 is substantially fixed, and the drive mechanism 126 is configured to rotate the radiation source 122 about a portion of the object 120 under examination. In this way, data from a variety of perspectives (e.g., tomosynthesis views) of the object 120 can be collected from a single scan of the object 120. It will also be appreciated that the ionizing radiation source 122 may emit radiation substantially continuously while its relative position is varied and/or radiation may be emitted intermittently (during source movement).

In one embodiment, the object scanning apparatus 102 is part of a mammography unit, and the object scanning apparatus 102 further comprises compression paddles 128 configured to compress the object 120 under examination. In this way, the object 120 (e.g., a human breast) is compressed to mitigate movement during the examination and/or reduce the distance radiation travels inside the object 120 (thereby improving image quality).

In the example scanner 100, the object scanning apparatus 102 is in operable communication with a pulse shaper 104 configured to shape detector signals (e.g., signals emitted by the detector when a photon is detected) and/or improve the characteristics of the detector signals, for example, using suitable analytical, iterative, or other shaping techniques. Additionally, a threshold determiner 106 may compare characteristics of the shaped detector signals, such as amplitude, to predetermined criteria and/or discard undesired portions of the signal (e.g., noise). For example, the threshold determiner 106 may discard signals that have amplitudes less than a predetermined threshold for the amplitude of desired signals (e.g., removing noise from desired signals).

Example scanner 100 also comprises a photon data processor 108 that is in operable communication with the threshold determiner 106. The photon data processor 108 is configured to receive a signal from the threshold determiner 106 (or the object scanning apparatus 102 if there is not a pulse shaper 104 and/or threshold determiner 106) and generate photon data indicative of the location and detection time of each of a plurality of photons detected by the detector 124 during the examination of the object 120. That is, the photon data processor 108 generates photon data relating to the x and y coordinate of the detector 124 for each of a plurality of photons that were detected by the detector 124 and also generates data relating to the time respective photons were detected by the detector 124.

The detection times of photons may correlate to exact (or otherwise substantially particular) positions of the ionizing radiation source 122 at those times. It will be appreciated that in some instances (because of practical limitations of the photon data processor 108), the photon data processor 108 may bin data related to the photons into acquisition bins based upon their respective detection times. For example, the photon data processor 108 may be unable to correlate each detected photon with a position of the ionizing radiation source 122 at the instance respective photons were emitted, so the photon data processor may bin the photons that were detected in a particular interval together and determine the position of the ionizing radiation source 122 during that interval of time. For example, in a five second examination, the photon data for a detected photon may be binned into one of a thousand different acquisition bins depending upon which five millisecond interval of time the photon was detected in (and representing photons emitted during a one millimeter span along the trajectory of the radiation source 122, for example). It will be understood to those skilled in the art that the number of acquisition bins should be relatively large (e.g., one thousand) to reduce tangential blurring (caused when each bin represents photons emitted during a larger span along the trajectory).

It will be appreciated that the photon data may indicate other characteristics of the detected photons as well. For example, the photon data may include information related to an energy of detected photons and/or a trajectory/angle of respective photons from the ionizing radiation source 122 to the detector 124 (based upon the location of the detected photon, the time it was detected, and the trajectory/location of the radiation source 122 at the instant the photon was detected). That is, the photon data processor 108 may correlate the detection time of the photons to a position of the radiation source 122 along a trajectory (at that time) to determine where each of the plurality of photons were emitted and then compare the radiation source's location to the respective detection locations to determine trajectories of the photons.

The example scanner 100 may further comprise a binner 110 that is in operable communication with the photon data processor 108 and configured to bin the photon data to produce binned projection data. The binner 110 may group the data based upon the detection times of the photons and/or the detection location of the photons. It will be appreciated that where the data was binned by the photon data processor 108 into acquisition bins, the data may be rebinned into a smaller number of bins (e.g., from one thousand acquisition bins to fifty bins). It will also be appreciated that the data may be filtered (through a low-pass filter) to avoid tangential blurring caused by grouping together a large amount of data (representing photons emitted over a relatively long segment (five millimeters) of the trajectory of the radiation source). The binner 110 then outputs the plurality of projections.

In one embodiment, the parameters for the binner 110 (e.g., number of bins, the method for binning (time, location, etc), etc.) may be adjusted. In one example, a user sets parameters for the binner 110 through a binning determiner 116. For example, the photon data may be binned into fifty temporal bins (each bin comprising data related to photons detected within a particular five millisecond period), and the user may change the number of temporal bins, causing the photon data to be rebinned accordingly.

It will be appreciated that the photon data (and/or the acquisition bins) produced by the photon data processor 108 may be stored in an object store so that the photon data may be rebinned at a later time (e.g., using different binning parameters). For example, a physician, reviewing the records of a patient three months later, may order the data to be rebinned into a larger number of temporal bins (to increase longitudinal resolution and more precisely determine the position of a malignant growth), and the data (and/or the acquisition bins) may be retrieved and rebinned according to the new parameters (e.g., changing the number of temporal bins from fifty to one hundred).

The illustrated example scanner 100 also comprises a tomosynthesis image reconstructor 112 that is operably coupled to the binner 110, and is configured to receive the binned projection data from the binner 110 and generate 2-D synthesized images indicative of the scanned object 120 using a suitable analytical, iterative, and/or other tomosynthesis reconstruction technique (e.g., similar to those currently used to convert projection data into tomosynthesized image data). The synthesized images may focus on various (non-overlapping) tomography planes (e.g., slices) of the object 120. In one example, the tomography planes depicted by the synthesized images are parallel to a plane formed by the detector 124.

The synthesized images may be presented in human perceptible form on a monitor 114 for human observation. It will be appreciated that by viewing a plurality of synthesized images depicting various tomography planes of the object, a virtually three-dimensional view of the object 120 may be formed by the user. In one embodiment, the monitor 114 displays a user interface configured to receive human input indicative of a number and/or location of tomosynthesis planes. The human input may be transmitted to a binning determiner 116, for example, to set parameters for the binner 110. Additionally, the user interface may be configured to receive human input indicative of operations for the object scanning apparatus 102, and a controller 118 may transmit the instructions to the object scanning apparatus 102.

Figure 2:
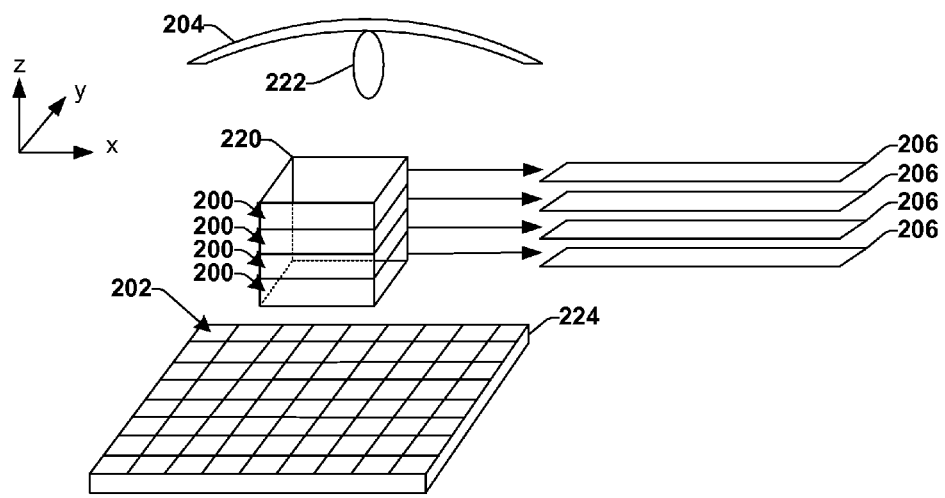
FIG. 2 illustrates example images that depict various tomography planes of an object based upon radiation that is detected on a photon counting detector.

FIG. 2 illustrates example images 206 that may depict various tomography planes 200 (e.g., horizontal slices) of an object 220 (e.g., 120 in FIG. 1) based upon radiation that is detected on a photon counting detector 224 (e.g., 124 in FIG. 1). The photon counting detector 224 is comprised of pixels 202 that are grouped together to form a detector plane (in the x and y direction) on the detector 224. Radiation that traverses the object 220 is detected by the pixels 202 of the detector 224.

The radiation is emitted from a radiation source 222 (e.g., 122 in FIG. 1). In the illustrated example, the radiation source 222 is attached to a guide mechanism 204 that allows the radiation source 222 to move along a predetermined trajectory (e.g., in the x direction). It will be understood to those skilled in the art that the radiation source 222 may emit radiation substantially continuously as it traverses the object. In this way, the power emitted by the radiation source 222 may be reduced since energy is emitted over a greater time period (relative to conventional pulse radiation techniques).

Two-dimensional images 206, depicting various tomography planes 200 (e.g., longitudinal ranges in the z direction) of the object 220, may be generated using reconstruction and tomosynthesis techniques. In the illustrated example, the tomography planes are parallel to the detector plane (in the x and y directions), and respective images represent one-fourth of the object's height in the z-direction. In this way, doctors may more accurately predict the z coordinate of a malignant growth, for example. It will be understood to those skilled in the art the tomography planes depicted in the actual images produced using the techniques herein described may not have such hard/sharp edges as illustrated in FIG. 2. That is, the tomography planes may merge slightly (e.g., the edge of one tomography plane may blend with the edge of another).

It will be understood to those skilled in the art that the number of tomography planes 200 (and therefore the images) that object 220 is divided into may be adjustable (e.g., by adjusting the number of bins a binner bins the photon data and/or acquisition bins into). For example, a user (e.g., a doctor) may vary the number of tomography planes 200 (after the data has been acquired) depending upon the desired resolution in the z-direction.

Figure 3:
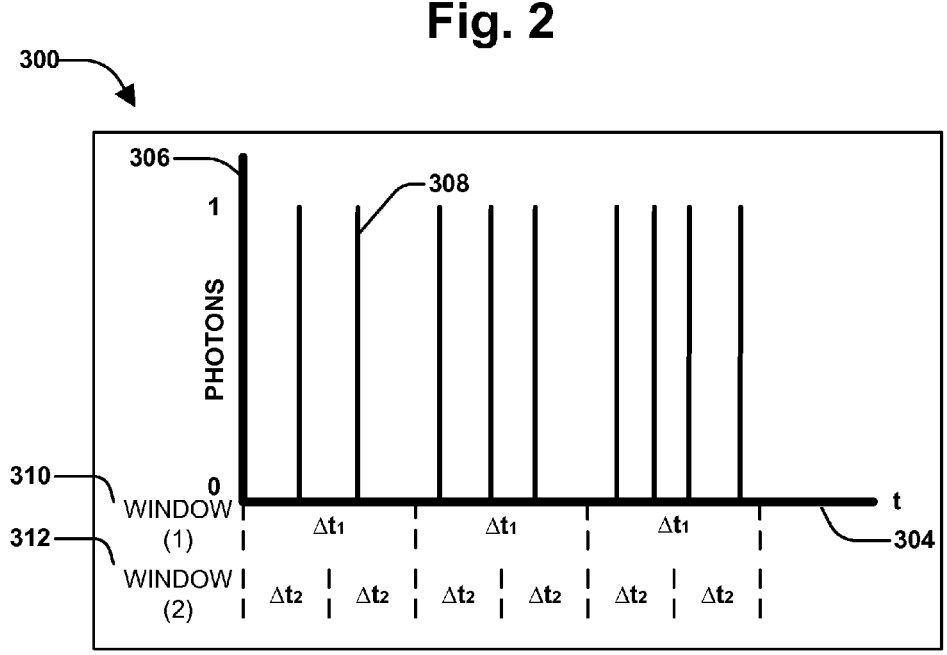
FIG. 3 is an example graph illustrating photon data that may be generated and binned for an arbitrary detector pixel comprised within a photon counting x-ray detector.

FIG. 3 is an example graph 300 illustrating photon data that may be generated and binned for an arbitrary detector pixel (e.g., 202 of FIG. 2) comprised within a photon counting x-ray detector (e.g., 224 in FIG. 2). The x-axis 304 illustrates time, and the y-axis 306 illustrates photons detected by the arbitrary detector pixel as a function of time. When a photon is detected by the arbitrary detector pixel, data related to the photon is generated by a photon data processor (e.g., 108 in FIG. 1) (and may be grouped with other photon data from other detectors that detected photons at substantially the same time (e.g., within a millisecond) into an acquisition bin). In the illustrated example graph 300, detected photons are represented by bars 308.

The photon data for the arbitrary detector pixel may be binned with similar data from other detector pixels by a binner (e.g., 110 in FIG. 1). In the illustrated example, the photon data and/or acquisition bins (if the photon data is grouped into acquisition bins) are binned (e.g., filtered and grouped and/or regrouped if the data was previously grouped into acquisition bins) as a function of time into a first plurality of temporal bins 310. For example, data related to photons detected in the first five milliseconds of the scan may be grouped into a first temporal bin, data related to photons detected between the fifth and tenth seconds of the scan may be grouped into a second temporal bin, etc. Additionally, the photon data may be rebinned (e.g., refiltered and regrouped) into a second plurality of bins (based upon a binning determiner similar to 116 in FIG. 1). In the illustrated example, the photon data is separated into a second plurality of temporal bins 312. It will be appreciated that the data may also and/or instead be binned based upon another data characteristic, such by a detected location (e.g., grouping data from predetermined detector pixels together). In the illustrated example, the bins depict equal time spans (e.g., five milliseconds of scanning in each bin), but it will be appreciated that the bins do not have to comprise equal sets of data (e.g., equal time spans, data from an equal number of pixels, etc.).

In one embodiment, the data is binned and/or rebinned based upon user input. For example, a user may designate a desired number of tomosynthesis planes, and the binning determiner may determine how to bin the data from a plurality of detector pixels. In one example, the binning determiner divides the total time of the scan by the desired number of tomosynthesis planes to determine the width of each bin (e.g., so that the temporal bins have an equal temporal width of two milliseconds and represent data related to photons that were emitted while a radiation source was in a particular portion of a predetermined trajectory that the radiation source traveled).

Figure 4:
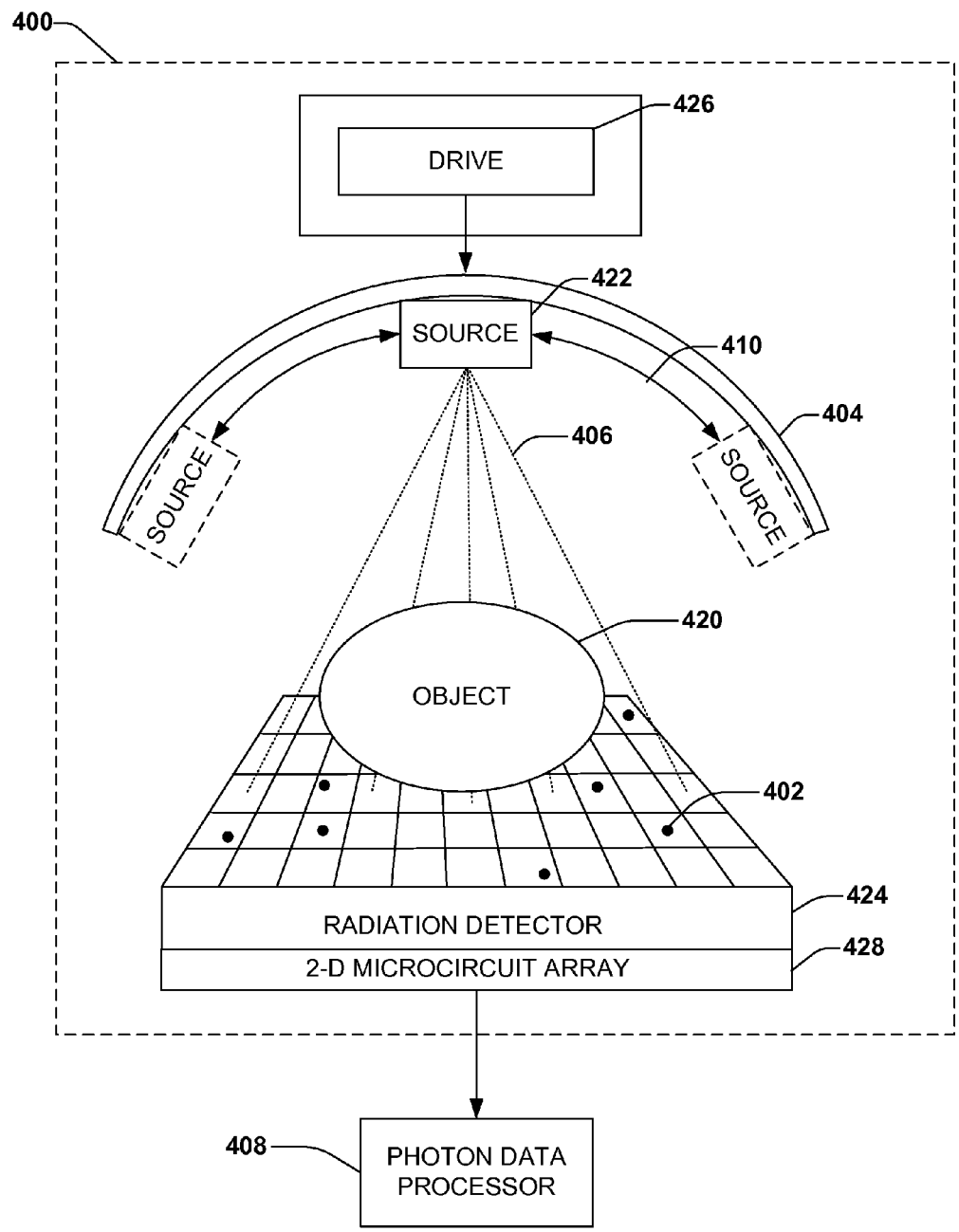
FIG. 4 is a cross sectional view of an example object scanning apparatus.

FIG. 4 is a cross sectional area (e.g., taken along line 4-4 in FIG. 1) of an example object scanning apparatus 400 (e.g., 102 in FIG. 1). The object scanning apparatus 400 comprises a radiation source 422 (e.g., 122 in FIG. 1) and a radiation detector 424 (e.g., 124 in FIG. 1) that vary relative to one another. The radiation source 422 may be affixed to a guide mechanism 404 (e.g., 204 in FIG. 2) that is configured to guide the radiation source 422 about a portion of an object 420 (e.g., 120 in FIG. 1) under examination (e.g., less than about sixty to about one hundred twenty degrees) based upon instructions and/or power from a drive mechanism 426 (e.g., 126 in FIG. 1).

In the illustrated example, the radiation source 422 follows a trajectory 410 about the object 420 and the radiation detector 424 is substantially stationary. However, other configurations are also contemplated. For example, the radiation detector 424 may rotate and the radiation source 422 may be substantially stationary. In another example, the radiation source 422 and the radiation detector 424 may both rotate, but their relative positions change.

Radiation 406 is emitted from the radiation source 422 and traverses the object 420 under examination. Photons (comprised within the radiation 406) that traverse the object 420 are detected by the radiation detector 424 (e.g., a pixilated photon counting detector) positioned on a diametrically opposing side of the object 420 from the radiation source 422. Detected photons (represented by small black dots 402) may be converted by a two-dimensional microcircuit array 428 into an electronic signal (capable of being processed).

The electronic signal may be transmitted from the object scanning apparatus 400 to a photon data processor 408 (e.g., 108 in FIG. 1) that is configured to process the signal and generate photon data indicative of the detected photons. For example, a photon data processor may generate photon data indicative of the location (on the radiation detector 424) of detected photons, detection times, etc for each of a plurality of detected photons. In one embodiment, the photon data processor 408 may also generate photon data indicative of a photon's trajectory by correlating the photon detection time to a position of the radiation source 422 at that instant. The process may be repeated from each of a plurality of other detected photons (relative to position(s) of the source 422).

It will be appreciated that were the photon data processor 408 is unable to determine the (substantially) exact position of the radiation source when each of the detected photons was emitted (because of processor limitations), the photon data processor 408 may bin photons detected at substantially the same instant (e.g., within the same millisecond) into one of a plurality of acquisition bins. In this way, the photon data processor 408 may determine the approximate position of the radiation source 422 for each of the plurality of acquisition bins (e.g., binning a first set of photon data in a first acquisition bin, the first set comprising data related to photons detected in a first millisecond of the examination and related to photons emitted while the radiation source 422 was traversing a first millimeter of the trajectory 410 and binning a second set of photon data in a second acquisition bin, the second set comprising data related to photons detected in a second millisecond of the examination and related to photons emitted while the radiation source 422 was traversing a second millimeter of the trajectory 410).

Figure 5:
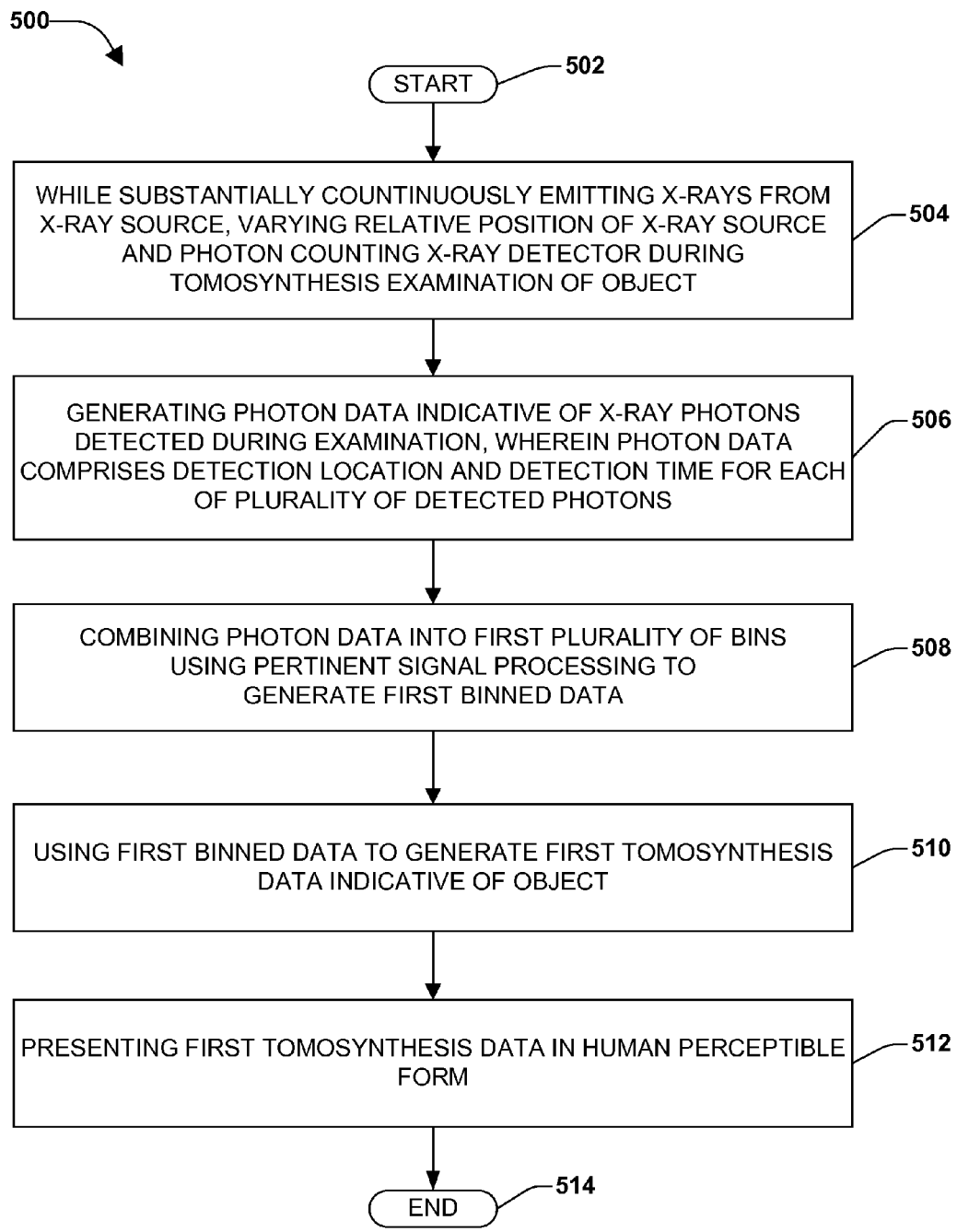
FIG. 5 is a flow diagram illustrating an example tomosynthesis method.

FIG. 5 illustrates an example method 500 of generating first tomosynthesis data indicative of an object (e.g., a human breast) under examination. The method begins at 502, and the relative position of an x-ray source and a photon counting x-ray detector is varied while substantially continuously emitting x-rays from the x-ray source during a tomosynthesis examination of the object at 504. In one embodiment, the x-ray source moves along a trajectory having central and distal portions. That is, the x-ray source may be centered on the object and repositioned so that it favors a portion of the object under examination. In another embodiment, the relative position of the x-ray source and the x-ray detector is varied through an angular range of less than about sixty to about one hundred twenty degrees (depending upon geometrical limitations of the scanning apparatus). It will be understood to those skilled in that art that other means of varying the relative position of the x-ray source and x-ray detector are also contemplated. For example, the x-ray source may be stationary while the x-ray detector rotates. Additionally, both the x-ray source and the x-ray detector may translate in a manner that causes their relative position to vary.

At 506, photon data indicative of x-ray photons detected during the examination is generated. The photon data comprises a detection location and a detection time for each of a plurality of the detected photons. For example, detected x-ray photons may be converted into signals and transmitted to a photon data processor configured to generate data indicative of the detection location (e.g., x,y coordinates of the position on the x-ray detector wherein the photon was detected) and detection time. It will be appreciated that the photon data may also comprise data related to other characteristics of the detected photons. For example, the photon data may also comprise a photon's energy for each of a plurality of the detected photons. It will be appreciated that the detection time may allow the relative position of the x-ray source when the photons were emitted to be determined for each of the detected photons. In one example, the detected photons may be binned into acquisition bins based upon their detection times, and the relative position of the x-ray source may be determined for each of a plurality of acquisition bins. It will be appreciated that the number of acquisition bins may be relatively large (e.g., 1000) so that each of the plurality of acquisition bins may comprise data related to photons detected in a relatively short time span (e.g., one millisecond) so that the acquisition bin represents photons emitted over a relatively small part of the trajectory (e.g., one millimeter of movement).

At 508, the photon data is combined into a first plurality of bins using pertinent signal processing to generate first binned (or combined) data. In one embodiment, the photon data is combined as a function of the characteristics (e.g., detection time, detection location, energy, etc.) of the detected photons. That is, the first plurality of bins may include temporal bins, spatial bins, and/or energy bins, for example, and the photon data for similar photons (e.g., photons having similar characteristics) may be grouped into one or more bins. In one example, the bins have an equal width. For example, the photon data may be combined into temporal bins, each bin of the first plurality of bins representing two milliseconds of the examination (e.g., bin one comprises photon data from photons detected in the first two milliseconds of the examination, bin two comprises photon data related to photons detected in the next two milliseconds of the examination, etc). It will be appreciated that the photon data may be filtered using pertinent signal processing (e.g., a low-pass filter) prior to being combined to reduce tangential blurring caused by combining into one bin photon data related to photons emitted over a relatively large part of the trajectory (e.g., six millimeters of the trajectory). It will be also appreciated that other combining techniques are also contemplated. For example, where the x-ray source and detector vary along a trajectory having central and distal portions, the bins related to photons emitted while nearer the central portion may have a shorter temporal width than bins related to photons emitted while nearer the distal portions.

In one embodiment, the bins are correlated with the x-ray source's relative position to create a plurality of tomosynthesis views. For example, a bin comprising photon data related to photons detected in the first two milliseconds of a scan may be correlated to the relative position of the radiation source during the first two milliseconds of the scan to form a tomosynthesis view (representing the object from a particular angular range). The process may be repeated for a second, third, etc. bin to form images from a plurality of tomosynthesis views.

It will understood to those skilled in the art that where the photon data is first divided into a plurality of acquisition bins, the photon data (and the acquisition bins) may be combined into a smaller number of bins. For example, one thousand acquisition bins may be combined into fifty bins (e.g., so that each bin comprises photon data related to twenty acquisition bins). It will be appreciated that not all of the data from the acquisition bins may be combined into the fifty bins. For example, some of the outlying data (after interpolation based upon a lo-pass filter) may be discarded to reduce tangential blurring caused by combining twenty acquisition bins into a single bin.

At 510, the first binned data is used to generate first tomosynthesis data indicative of the object. That is, data from the respective bins of the plurality of bins are grouped and/or filtered through analytic, iterative, or other tomosynthesis and/or reconstruction techniques to form 2-D synthesized images depicting a plurality of tomosynthesis planes of the object under examination. It will be appreciated that the number of synthesized images may be a function of the number of bins comprising the plurality of bins (e.g., four bins may generate four synthesized images, fifty bins may generate fifty synthesized images, etc.).

In one embodiment, the acts of combining and using may be repeated to combine the photon data into a second plurality of bins and generate second tomosynthesis data indicative of the object. In this way, the number of synthesized images may be increased and/or decreased. For example, the first plurality of bins and the second plurality of bins may comprise data sorted according the similar parameters (e.g., time), but the width of bins comprised in the second plurality of bins may be different than the width of bins in the first plurality (to improve image quality and/or narrow the longitudinal height of the tomography plane). It will be understood to those skilled in the art that other parameters for recombining and reusing are also contemplated. For example, the second plurality of bins may be similar to the first plurality of bins (e.g., the first and second plurality of bins may be temporal bins comprising data related to two millisecond intervals of detected photons), but the second plurality of bins may be offset (e.g., by one millisecond) from the first plurality of bins (so that tomosynthesis planes of the second plurality are offset from tomosynthesis planes of the first plurality). In another example, the organization of the photon data in the second plurality of bins may be different than the organization of the photon data in the first plurality of bins (e.g., the first plurality of bins may be organized temporally and the second plurality of bins may be organized by detection location).

At 512, the first (or the second) tomosynthesis data is presented in human perceptible form. Various synthesized 2-D images may depict various tomosynthesis planes of the object. For example, a first synthesized image may depict targets comprised in a bottom region of the object under examination and a second synthesized image may depict targets comprised in an upper region. If a large number of synthesized images are created (e.g., 50 images), and the various images depict unique regions (e.g., tomosynthesis planes) of the object, a virtually three-dimensional view of the object may be formed. The method ends at 514.

Figure 6:
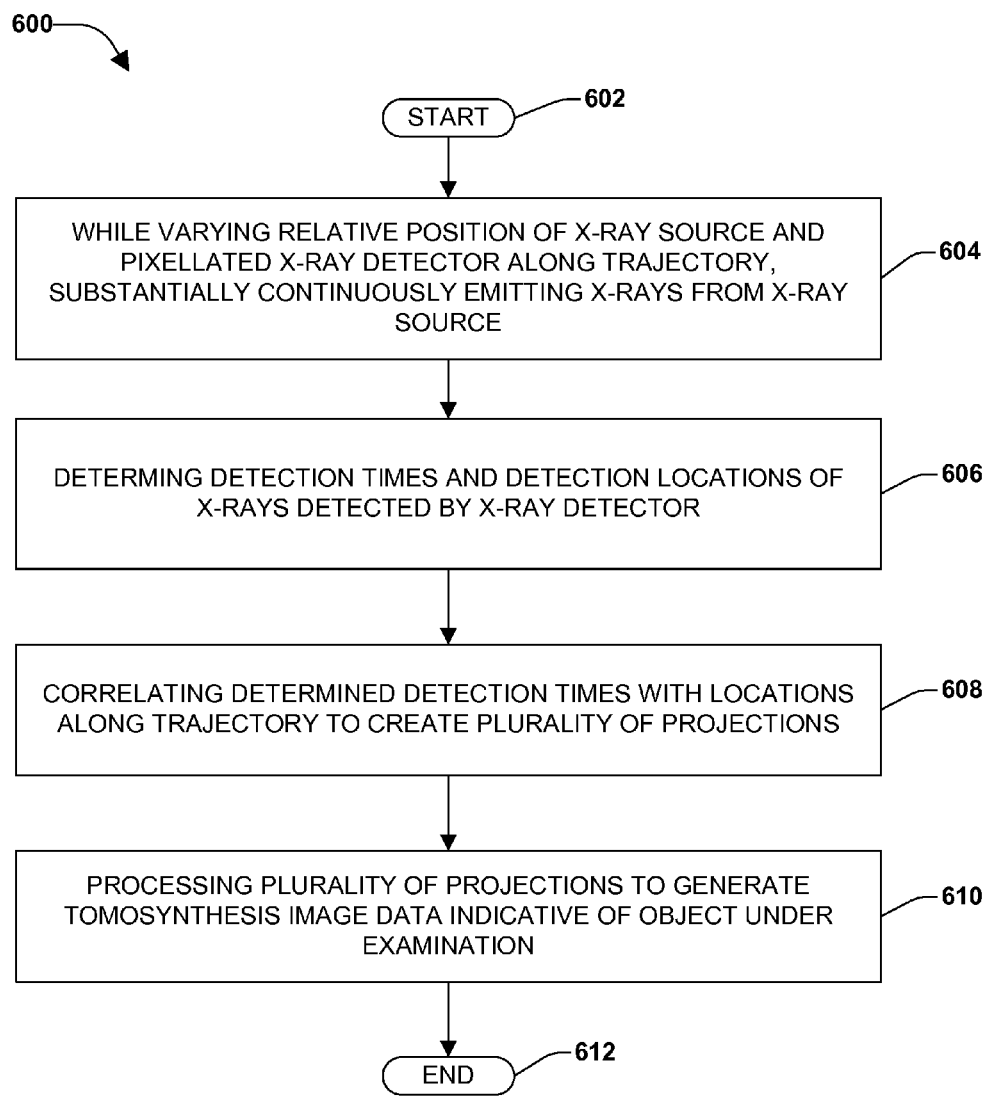
FIG. 6 is a flow diagram illustrating an example method of generating tomosynthesis image data.

FIG. 6 illustrates an example method 600 for generating tomosynthesis image data. The method begins at 602, and, while varying the relative position of an x-ray source and a pixelated x-ray detector along a trajectory, x-rays are substantially continuously emitted from the x-ray source at 604. That is, the x-ray source and/or the x-ray detector are rotated in such a manner that their relative position to one another changes. In general, their relative position may have an angular change less than about sixty to about one hundred twenty degrees, but other angular changes are contemplated as well. It will be appreciated that the x-ray source and the x-ray detector may move independently of one another and/or in cooperation with one another.

At 606, detection times and detection locations of x-rays detected by the x-ray detector are determined. In one embodiment, a photon data processor receives a signal from the x-ray detector when an x-ray photon is detected and the photon data processor determines the detection time and detection location (e.g., the coordinates of the pixel on the pixelated x-ray detector that detected the photon). It will be understood that other characteristics (other than detection time and detection location) may also be determined. For example, the detection angles and/or the energies of the detected photons may be determined.

At 608, the determined detection times are correlated with locations along the trajectory to create a plurality of projections. That is, the relative position of the x-ray source and the x-ray detector may be known, and, based upon the detection time of a photon, the relative position of the x-ray source and x-ray detector at the instant the detected photon was emitted can be determined. Using this determined relative position, and the detection location of the photon, the trajectory of the photon from the x-ray source to the x-ray detector may be determined. In one embodiment, groups of photons (and corresponding photon data) may be binned into acquisition bins based upon a time interval in which the photons were detected (e.g., photons detected in the first millisecond of the scan may be grouped into one acquisition bin, photons detected in the second millisecond of the scan may be grouped into a second acquisition bin, etc). The photon data related to the photons and/or the acquisition bins, may be filtered (through a lo-pass filter) and binned (or rebinned if the photon data has already been binned into acquisition bins). In one example, data related to photons that were emitted from a similar first position may be binned together to form a first projection, and a second projection may be formed based upon data related to photons that were emitted from a similar second position. In this way, a plurality of projections may be created.

At 610, the plurality of projections is processed to generate tomosynthesis data indicative of an object under examination. In one embodiment, the projections are reconstructed into two-dimensional (2-D) images and undergo tomosynthesis using suitable analytic or iterative techniques. It will be appreciated that synthesized images (e.g., images produced after tomosynthesis) may represent various tomography planes of the object under examination. It will also be appreciated that the number of tomography planes represented may be a function of the number of projections created. For example, if the data is separated into five projections, five tomosynthesis images (representing five tomography planes of the object) may be created.

It will be understood to those skilled in the art that the techniques herein described offer numerous benefits over techniques currently used in the art. For example, the quality of an equivalent number of synthesized images may be improved using the techniques herein described. The signal-to-noise ratio is relatively insignificant using the techniques herein disclosed so the overall dose of radiation to the object may be spread over a larger angular range (e.g., less than about sixty to about one hundred twenty degrees). Additionally, the tomography planes are not a function of a number of tomosynthesis views and/or the angular spacing between views because radiation may be substantially continuously emitted. Rather, data may be acquired at essentially an infinite number of points along the trajectory and binned according to a plurality of different characteristics to produce tomography planes of the object. Therefore, artifacts caused by larger angular ranges (e.g., over two degrees) may be mitigated.

The image quality may further be improved using the techniques herein described by mitigating tangential blurring caused by a virtual "elongation" of the focal spot and/or reducing the size of the focal spot (by binning the photon data into acquisition bins and/or through low-pass filtering). The photons are counted, rather than their energy measured, so the virtual "elongation" of the focal spot does not affect the data used to create the projections (and therefore the images ultimately produced). Additionally the power to the radiation source may be reduced (e.g., causing the size of the focal spot to be reduced and the image quality to be improved, while also reducing costs) because radiation may be substantially continuously emitted.

The techniques herein described may also decrease the time of the examination because the relative position of the radiation source and the detector may be varied at a faster rate. Using current techniques, the rate at which the radiation source and/or the detector are varied is limited by the virtual "elongation" that is created when the relative position is varied too rapidly. Since the techniques herein described count photons, the relative position of the radiation source and the detector may be varied more rapidly. In mammography scans, for example, this may be particularly beneficial since the breast is often placed in a compressed (and uncomfortable) state.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:
1. A method, comprising:
performing a tomosynthesis examination of an object by varying a relative position between an ionizing radiation source and a photon counting detector;

generating photon data indicative of radiation photons detected during the tomosynthesis examination, the photon data comprising a detection location and a detection time for at least some of the radiation photons detected during the tomosynthesis examination;

combining the photon data into a first plurality of temporal bins to generate first binned data, comprising:

combining first photon data indicative of a first set of radiation photons detected during a first temporal range of the tomosynthesis examination into a first bin of the first plurality of temporal bins; and combining second photon data indicative of a second set of radiation photons detected during a second temporal range of the tomosynthesis examination into a second bin of the first plurality of temporal bins; and using the first binned data to generate first tomosynthesis data indicative of the object.

2. The method of claim 1, the performing comprising: examining the object over a limited view-angle.

3. The method of claim 2, the limited view-angle being a view-angle of less than about 360 degrees.

4. The method of claim 2, the limited view-angle being a view-angle of less than about 180 degrees.

5. The method of claim 2, the limited view-angle being a view-angle of less than about 60 degrees.

6. The method of claim 1, a temporal width of the first temporal range different than a temporal width of the second temporal range.

7. The method of claim 1, comprising:
recombining the photon data into a second plurality of bins to generate second binned data; and
using the second binned data to generate second tomosynthesis data indicative of the object, the second tomosynthesis data different than the first tomosynthesis data.

8. The method of claim 1, the photon data comprising a photon energy for the at least some of the radiation photons detected during the tomosynthesis examination.

9. An apparatus, comprising:
an examination region configured to selectively receive an object under examination;
an ionizing radiation source configured to emit radiation photons into the examination region;
a photon counting detector configured to detect radiation photons that have traversed the object;
a drive configured to vary a relative position between the ionizing radiation source and the photon-counting detector by moving the ionizing radiation source along a trajectory; and
a photon data processor configured to generate photon data indicative of a detection location and a detection time of at least some of the radiation photons detected by the photon-counting detector and to correlate a first detection time of a first radiation photon detected by the photon-counting detector with a location of the ionizing radiation source along the trajectory at a time when the first radiation photon was emitted from the ionizing radiation source.

10. The apparatus of claim 9, the drive configured to vary the relative position between the ionizing radiation source and the photon-counting detector by less than about 60 degrees.

11. The apparatus of claim 9, comprising a binner configured to combine the photon data into a first plurality of bins to generate first binned data.

12. The apparatus of claim 11, the binner configured to combine the photon data according to criteria specified by a user.

13. The apparatus of claim 9, comprising:
a binner configured to combine the photon data into a first plurality of bins to generate first binned data and to combine the photon data into a second plurality of bins to generate second binned data; and
an image reconstructor configured to generate a first image of the object using the first binned data and to generate a second image of the object using the second binned data.

14. The apparatus of claim 9, the photon counting detector comprising a direct conversion detector material configured to convert radiation photons directly into electrical charge.

15. A method of generating tomosynthesis image data, comprising:
emitting radiation from an ionizing radiation source while varying, along a trajectory, a relative position between the ionizing radiation source and a pixelated detector;
determining detection times and detection locations of at least some radiation detected by the pixelated detector;
correlating the detection times with locations along the trajectory to create a first plurality of projections; and
processing the first plurality of projections to generate tomosynthesis image data indicative of an object under examination.

16. The method of claim 15, the varying comprising:
moving the ionizing radiation source relative to the object while maintaining a relative position between the pixelated detector and the object.

17. The method of claim 16, the moving comprising:
moving the ionizing radiation source over a limited view-angle, the view-angle being less than about 60 degrees.

18. The method of claim 15, the ionizing radiation source comprising an x-ray source.

19. The method of claim 15, the determining comprising:
determining photon energies of the at least some radiation detected by the pixelated detector.

20. The method of claim 15, the tomosynthesis image data indicative of a two-dimensional image of the object.

* * * * *